(12) United States Patent
Buckley et al.

(10) Patent No.: US 9,446,079 B2
(45) Date of Patent: Sep. 20, 2016

(54) HONEY AND SILVER NITRATE COMPOSITION, COMPOSITION DRESSING AND METHODS OF MAKING SAME

(71) Applicant: LINKS MEDICAL PRODUCTS INCORPORATED, Irvine, CA (US)

(72) Inventors: Thomas L. Buckley, Laguna Niguel, CA (US); Andrew Thain, Staffordshire (GB)

(73) Assignee: Links Medical Products, Incorporated, Irvine, CA (US)

( * ) Notice: Subject to any disclaimer, the term of this patent is extended or adjusted under 35 U.S.C. 154(b) by 0 days.

(21) Appl. No.: 14/824,134

(22) Filed: Aug. 12, 2015

(65) Prior Publication Data
US 2015/0343001 A1 Dec. 3, 2015

Related U.S. Application Data

(63) Continuation-in-part of application No. 14/642,664, filed on Mar. 9, 2015, now Pat. No. 9,107,974, which is a continuation-in-part of application No. 29/511,393, filed on Dec. 10, 2014, now Pat. No. Des. 745,690, and a continuation-in-part of application No. 13/939,829, filed on Jul. 11, 2013.

(51) Int. Cl.
*A61F 13/15* (2006.01)
*A61K 35/644* (2015.01)
(Continued)

(52) U.S. Cl.
CPC ....... *A61K 35/644* (2013.01); *A61F 13/00063* (2013.01); *A61F 13/0289* (2013.01); *A61K 9/06* (2013.01); *A61K 31/121* (2013.01); *A61K 33/38* (2013.01); *A61L 15/18* (2013.01); *A61L 15/40* (2013.01); *A61L 15/425* (2013.01);
(Continued)

(58) Field of Classification Search
CPC ..... A61K 33/38; A61K 33/00; A61M 27/00; A61L 15/16; A61F 2013/0091; A61F 2013/00927; A61F 2013/00936; A61F 2013/00089; A61F 2013/00331; A61F 13/00
USPC .......................... 604/360, 543; 424/443–447
See application file for complete search history.

(56) References Cited

U.S. PATENT DOCUMENTS

| | | |
|---|---|---|
| 5,785,972 A | 7/1998 | Tyler |
| 6,379,712 B1 | 4/2002 | Yan et al. |

(Continued)

OTHER PUBLICATIONS

Scott Bolhack, et al. "Complications from the Use of Silver Nitrate on Wounds with Cellulose Dressings", www.healthcarecompanies.com.
International Consensus. Appropriate Use of Silver Dressings in Wounds. An Expert Working Group Consensus. London: Wounds International, 2012.

(Continued)

*Primary Examiner* — Jacqueline Stephens
(74) *Attorney, Agent, or Firm* — Jerry R. Putts; James R. McDaniel

(57) ABSTRACT

A composition of medical grade honey and silver nitrate is described for treatment of burns, ulcers, and open wounds. The disclosed composition is a gel of medical grade honey and silver nitrate in a ratio of about 211 to 1, with a moisture level of no greater than 20 percent and wherein the medical grade honey contains about 300 kg/mg of methylglyoxal. Also described are methods of making and using the honey and silver nitrate mixture for treatment of burns, ulcers and wounds including direct application to a treatment area as well as impregnating a gauze fabric with a composition of medical grade honey and silver nitrate for application to a treatment area.

16 Claims, 3 Drawing Sheets

(51) Int. Cl.
- *A61K 33/38* (2006.01)
- *A61K 9/06* (2006.01)
- *A61K 31/121* (2006.01)
- *B65B 3/04* (2006.01)
- *A61F 13/02* (2006.01)
- *A61L 15/40* (2006.01)
- *A61L 15/42* (2006.01)
- *A61L 15/60* (2006.01)
- *A61L 15/18* (2006.01)
- *A61F 13/00* (2006.01)

(52) U.S. Cl.
CPC ............ *A61L 15/60* (2013.01); *B65B 3/04* (2013.01); *A61F 2013/00089* (2013.01); *A61F 2013/0091* (2013.01); *A61F 2013/00314* (2013.01); *A61F 2013/00331* (2013.01); *Y10T 156/1052* (2015.01)

(56) References Cited

U.S. PATENT DOCUMENTS

| | | |
|---|---|---|
| 8,623,335 B2 | 1/2014 | Waddington |
| 8,852,648 B2 | 10/2014 | Salamone et al. |
| 8,920,848 B2 | 12/2014 | Gammelsaeter et al. |
| 8,946,317 B2 | 2/2015 | Asada et al. |
| 2008/0299220 A1* | 12/2008 | Tamarkin ............ A61K 9/0014 424/600 |
| 2012/0021061 A1* | 1/2012 | Schlothauer ............ A23L 1/08 424/537 |
| 2015/0037388 A1 | 2/2015 | Longo |

OTHER PUBLICATIONS

Rose Cooper, "A Review of the Evidence for the Use of Topical Antimicrobial Agents in Wound Care," Worldwide Wounds, Feb. 2004.

Steve Thomas, "MRSA and the Use of Silver Dressings: Overcoming Bacterial Resistance," Worldwide Wounds, Nov. 2014.

* cited by examiner

HONEY AND SILVER NITRATE COMPOSITION, COMPOSITION DRESSING AND METHODS OF MAKING SAME

RELATED APPLICATIONS

The present application is a continuation-in-part of U.S. patent application Ser. No. 14/642,664, now U.S. Pat. No. 9,107,974, which is incorporated herein by reference as though fully set forth.

FIELD OF THE INVENTION

The present invention is generally directed to wound, ulcer and burn treatment medicines, and more particularly to a composition comprising a gel mixture of honey and silver nitrate and methods of making and using the composition for the treatment of wounds, ulcers and burns.

BACKGROUND OF THE INVENTION

Prior to the present invention, as set forth in general terms above and more specifically below, it is known, to employ various antibacterial and antiseptic compounds and compositions for the treatment or therapy for burns, ulcers and open wounds. See for example, U.S. Pat. No. 5,785,972 by Tyler, U.S. Pat. No. 6,379,712 by Yan et al., U.S. Pat. No. 8,623,335 by Waddington, U.S. Pat. No. 8,852,648 by Salamone et al., U.S. Pat. No. 8,920,848 by Gammelsaeter et al., U.S. Pat. No. 8,946,317 by Asada et al., and U.S. Patent Application Publication 2015/0037388 by Longo. While these various wound dressings, compounds and compositions may have been generally satisfactory, there is nevertheless a need for a new and improved composition which can be directly applied to wounds and wound dressings to provide powerful antibacterial forces on infected wounds and protection from outside sources of biological contamination.

It is a purpose of this invention to fulfill this and other needs in the medicine art in a manner more apparent to the skilled artisan once given the following disclosure.

BRIEF SUMMARY OF THE INVENTION

A first aspect of the present invention is a honey and silver nitrate composition for treating wounds, comprising a mixture of honey and silver nitrate in a honey to silver nitrate ratio preferably in a range of between about 85:1 and about 1000:1 and more preferably in a range of between about 200:1 and about 350:to 1, and most preferably in a range of between about 200 to 1 and 250 to 1 and wherein the moisture content of the mixture of honey and silver nitrate is no greater than twenty percent.

In one embodiment of the first aspect of the present invention the honey and silver nitrate composition has a honey to silver nitrate ratio of 211 to 1.

In another embodiment of the first aspect of the present invention, the honey in the honey and silver nitrate composition is a medical grade honey which contains a preferred amount of methylglyoxal of between about 1.0 mg/kg of methylglyoxal and about 4000 mg/kg of methylglyoxal, and a more preferred amount of methylglyoxal of between about 83 mg/kg of methylglyoxal and about 400 mg/kg of methylglyoxal, and a most preferred amount of methylglyoxal of between about 300 mg/kg of methylglyoxal and about 350 mg/kg of methylglyoxal.

In another embodiment of the first aspect of the present invention, the medical grade honey in the honey silver nitrate composition contains 300 mg/kg of methylglyoxal.

In yet another embodiment of the first aspect of the present invention, the medical grade honey is selected from the group consisting of Manuka, Pasture, Ling Kahami, Portobello, Greek Pine, Yorkshire, Chilean Ulmo, Chilean Rain Forrest, Australian *Eucalyptus*, Himalayan, Scottish Heather, Scottish Wild Flower, English Heather, English Wildflower, New Zealand Clover, Australian Clover, Cuban Comparitan, *Acacia*, Spanish Blossom, Tasmanian Leatherwood, Organic Honey All, New Zealand Beach, Kanuka, New Zealand Bush, New Zealand Honey Dew, Jarrah, Thyme, Kamahi and *Leptospermum* honeys of all varieties.

In still yet another embodiment of the first aspect of the present invention, the honey and silver nitrate composition is a gel.

A second aspect of the present invention is a method of preparing a honey and silver nitrate composition for treating burns, ulcers and wounds, comprising the steps of: heating an amount of honey; blending an amount of silver nitrate with the amount of honey to provide a honey to silver nitrate ratio of between about 200 to 1 and about 250 to 1; placing the honey and the silver nitrate into a high speed mixer; and mixing the honey and the silver nitrate in the mixer until a fully homogenized composition of honey and silver nitrate is achieved.

In one embodiment of the second aspect of the present invention, the method further includes the step of heating the honey to 30° C.

In another embodiment of the second aspect of the present invention, the method further includes the step of pumping the honey and silver nitrate composition into a holding container for bulk shipping to a tube or dressing converter.

In another embodiment of the first aspect of the present invention, the honey in the honey and silver nitrate composition is a medical grade honey which contains a preferred amount of methylglyoxal of between about 1.0 mg/kg of methylglyoxal and about 4000 mg/kg of methylglyoxal, and a more preferred amount of methylglyoxal of between about 83 mg/kg of methylglyoxal and about 400 mg/kg of methylglyoxal, and a most preferred amount of methylglyoxal of between about 300 mg/kg of methylglyoxal and about 350 mg/kg of methylglyoxal.

In still another embodiment of the second aspect of the present invention, the honey is selected from the group including medical grade Manuka, Pasture, Ling Kahami, Portobello, Greek Pine, Yorkshire, Chilean Ulmo, Chilean Rain Forrest, Australian *Eucalyptus*, Himalayan, Scottish Heather, Scottish Wild Flower, English Heather, English Wildflower, New Zealand Clover, Australian Clover, Cuban Comparitan, *Acacia*, Spanish Blossom, Tasmanian Leatherwood, Organic Honey All, New Zealand Beach, Kanuka, New Zealand Bush, New Zealand Honey Dew. Jarrah, Thyme, Kamahi and *Leptospermum* honeys of all varieties.

A third aspect of the present invention is a honey and silver nitrate wound dressing, comprising a base dressing material, such as a base gauze material or a base foam material, impregnated or dosed with a honey and silver nitrate composition, wherein the honey and silver nitrate composition has a honey to silver nitrate ratio of between about 200 to 1 and about 250 to 1 and wherein the moisture content of the honey and silver nitrate composition is no greater than about twenty percent.

In one embodiment of the third aspect of the present invention, the honey and silver nitrate composition includes a medical grade honey which contains a preferred amount of methylglyoxal of between about 1.0 mg/kg of methylglyoxal and about 4000 mg/kg of methylglyoxal, and a more preferred amount of methylglyoxal of between about 83 mg/kg of methylglyoxal and about 400 mg/kg of methylglyoxal, and a most preferred amount of methylglyoxal of between about 300 mg/kg of methylglyoxal and about 350 mg/kg of methylglyoxal.

In another embodiment of the third aspect of the present invention, the medical grade honey is selected from the group consisting of Manuka, Pasture, Ling Kahami, Portobello, Greek Pine, Yorkshire, Chilean Ulmo, Chilean Rain Forrest, Australian *Eucalyptus*, Himalayan, Scottish Heather, Scottish Wild Flower, English Heather, English Wildflower, New Zealand Clover, Australian Clover, Cuban Comparitan, *Acacia*, Spanish Blossom, Tasmanian Leatherwood, Organic Honey All, New Zealand Beach, Kanuka, New Zealand Bush, New Zealand Honey Dew, Jarrah, Thyme, and Kamahi and *Leptospermum* honeys of all varieties.

In still yet another embodiment of the third aspect of the present invention, the honey and silver nitrate composition is a gel.

In still another embodiment of the third aspect of the present invention, a weight of the honey and silver nitrate dose is between about 51% and about 67% of the total dressing weight.

The preferred honey and silver nitrate composition and impregnated medical dressing, according to various embodiments of the present invention, offer the following advantages: ease of use of the composition for direct application to wounds and wound dressings; excellent light and heat stability of the composition; excellent anti-bacterial activity of the composition; excellent hygroscopic characteristics of the composition; the ability of the composition to provide nutrients to the wound bed; excellent anti-inflammatory characteristics of the composition; excellent pain relieving characteristics of the composition; reduced healing time of the wound; excellent debridement characteristics of the composition; increased antimicrobial characteristics of the composition; improved odor control by the composition; and excellent osmotic absorption of excess exudate by the dressing during treatment. In fact, in many of the preferred embodiments, these advantages are optimized to an extent that is considerably higher than heretofore achieved in prior, known compositions and dressings.

BRIEF DESCRIPTION OF THE DRAWINGS

The above mentioned features and steps of the invention and the manner of attaining them will become apparent, and the invention itself will be best understood by reference to the following description of the embodiments of the invention in conjunction with the accompanying drawings, wherein like characters represent like parts throughout the several views and in which.

DETAILED DESCRIPTION OF THE PREFERRED EMBODIMENTS OF THE INVENTION

Figure 3:
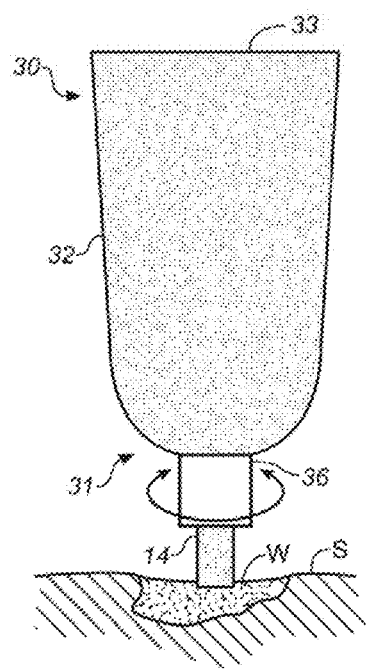
FIG. 3 is a schematic drawing of a tube which contains a volume of a composition of honey and silver nitrate being directly applied to a wound, according to the present invention.
Figure 4:
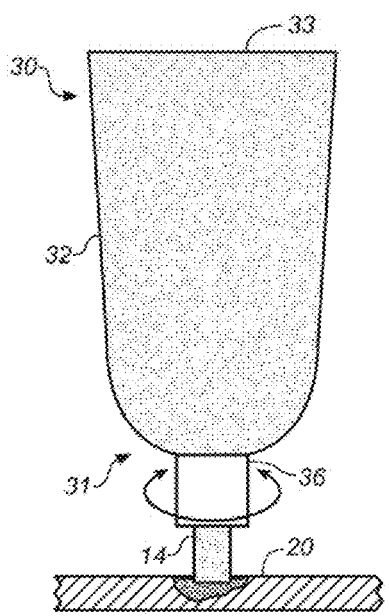
FIG. 4 is a schematic drawing of a tube which contains a volume of a composition of honey and silver nitrate being directly applied to a dressing material for application to a wound, according to the present invention.

Referring now to the drawings and more particularly to FIGS. 3 and 4, there is illustrated a honey silver nitrate composition 14, which is prepared in accordance with the present invention. As will be explained hereinafter in greater detail, the honey silver nitrate composition 14 is prepared to provide antimicrobial, antibacterial and healing properties through the natural osmotic properties found in the honey silver nitrate composition 14. As will be explained hereinafter in greater detail, the synergistic effect of the combination of medical grade honey and silver nitrate in a preferred honey to silver nitrate ratio of between about 50 to 1 and about 1000 to 1, a more preferred ratio of between about 200 to 1 and about 250 to 1, with a most preferred ratio of about 211 to 1 provides an unexpected antibacterial effect which is substantially greater than the antibacterial effect of either component taken alone when applied to a wound.

With respect to the presently disclosed invention, the following should be considered relative to the honey component of the composition 14. That is, honey is known to have a high osmolarity and solutions of high osmolarity are also known to cause the removal of water molecules from blood cell. In this regard, the outflow of lymph fluids created by the osmotic action of honey is beneficial to a healing process. This type of healing process is known as autolytic debridement. In short then, the outflow of liquid from a wound washes bacteria and dead wound cells to the surface and thus, into direct contact with the antibacterial honey and silver nitrate compound 14 promotes accelerated wound healing.

The honey component of the present invention is preferably medical grade honey which means it may be directly applied to an ulcer, a burn or an open wound. In this regard, the honey component that is used is preferably sterile honey which is obtained by subjecting raw honey to a sterilization process, such as subjecting the raw honey to gamma rays. Sterilized honey, even after such radiation, retains its antibacterial activity which is a result of its high sugar content, low pH, enzymic production of hydrogen peroxide and extra plan florally-derived factors found in honey having a certain amount of methylglyoxal.

Honey, containing preferably at least 1.0 to 4000 mg/kg of methylglyoxal and more preferably at least 83.0 mg/kg to 400 mg/kg of methylglyoxal and most preferably at least 300 mg/kg to 350 mg/kg of methylglyoxal plays an important wound healing role in managing infected wounds when mixed with a silver salt, such as silver nitrate whether applied alone or used in conjunction with appropriate dressings. Honey when mixed with silver nitrate provides powerful antibacterial factors on infected wounds. Honey in this combination inherently has a number of properties that lend it for use in wound care dressings. First, honey is light- and heat-stable such that honey is not influenced by conventional sterilizing procedures. Second, honey exhibits an osmotic absorption of excess exudate. Third, honey exhibits an anti-bacterial activity that can inhibit the growth of bacteria and limit the production of the undesirable bi-products of bacterial growth. Fourth, honey is hygroscopic which means it is capable of absorbing moisture from the air which, in turn, allows honey to be used effectively in moist wound care. Fifth, honey provides beneficial nutrients to the wound bed. Sixth, the anti-inflammatory characteristics of honey hasten the healing of wounds. Seventh, honey can be used as a pain reliever due to the high sugar content in honey in that honey prevents pain during dressing changes because honey keeps the wound surface moist by mobilizing the edema from the surrounding tissues. Eighth, honey can be used as a pain reliever by de-sensitizing the nerve endings due to inflammation. Ninth, the low pH level of honey helps to reduce wound healing time by increasing the amount of oxygen off-loaded from hemoglobin in the capillaries in a wound area. Tenth, honey provides an autolytic debridement characteristic by removing bacteria creating slough. Eleventh, honey has high osmolarity (the concentration of an osmotically active substance in solution) which causes removal of water molecules from cells. Twelfth, honey creates an enzymic production of hydrogen peroxide. Finally, honey reduces the malodor from wound beds. When the term "honey" is utilized in this specification it means a "medical grade honey" which has been standardized through gamma irradiation, filtration, and lab-controlled conditions to ensure that the honey is free of contaminates.

With reference to the present invention, it was found that the most preferred honeys were selected from a group of honeys consisting of Manuka, Pasture, Ling Kahami, Portobello, Greek Pine, Yorkshire, Chilean Ulmo, Chilean Rain Forrest, Australian *Eucalyptus*, Himalayan, Scottish Heather, Scottish Wild Flower, English Heather, English Wildflower, New Zealand Clover, Australian Clover, Cuban Comparitan, *Acacia*, Spanish Blossom, Tasmanian Leatherwood, Organic Honey All, New Zealand Beach, Kanuka, New Zealand Bush, New Zealand Honey Dew, Jarrah, Thyme, Kamahi and *Leptospermum* honeys of all varieties. Each of the above-mentioned honeys are all known to contain superior anti-bacterial and anti-inflammatory effects and thus, are preferred honeys for the composition 14.

Regardless of which honey is selected from the above-mentioned group for use in the honey silver nitrate composition 14, it should be understood that one of the more important considerations for honey selection is that the selected honey must contain a sufficient amount of methylglyoxal to provide the benefits heretofore mentioned. A sufficient amount has been determined to be preferably between about 1.0 and 1400 mg/kg of methylglyoxal. A more preferable amount of methylglyoxal is about 83.0 to 400 mg/kg of methylglyoxal and a most preferred amount is about 300 to 350 mg/kg of methylglyoxal. For clarity purposes, methylglyoxal is also sometimes called pyruvaldehyde or 2-oxopropanal, which is an organic compound expressed by the formula $CH_3C(O)CHO$.

Considering now the silver ion component of the present invention, it has been determined by experimentation that the silver ions of silver nitrate in combination with a medical grade honey provides amplified antibacterial activities. The silver nitrate having an oligodynamic effect which is toxic for bacterial, algae, and fungi in vitro. The antibacterial action of silver in this instance is dependent on the silver ions. More particularly, the silver ion ($Ag+$) is bioactive and when present in a sufficient concentration it readily kills bacteria in vitro. The effectiveness of a silver compound as an antiseptic is based on the ability of the biologically active silver ion ($Ag+$) within the compound to irreversibly damage key enzyme systems in the cell membranes of pathogens.

While several different salts of silver were considered for the composition of the present invention, silver nitrate was preferred because it is one of the most, if not the most, soluble of the silver salts. This characteristic is an important feature of the present invention as it facilitates the ability to incorporate a sufficient quantity of the salt into the selected honey whilst maintaining a honey moisture content at or below 20 percent. This is a critical level since it will substantially prevent the growth of mold, mildew, fungus and yeast. In short, the solubility of silver nitrate is an important feature of the present invention relative to providing a compound with effective antimicrobial qualities.

Considering now the silver nitrate component of the present invention in greater detail, silver nitrate is provided as a silver salt with a preferred range of purity from between about 50% and about 99% pure. The most preferred silver salt is +99% pure as the silver nitrate operates to keep the moisture level of the honey silver nitrate composition at or below 20 percent, which is as already noted a very important feature of the present invention.

Once the silver salt is obtained it is mixed with sterile water to create a correct concentration for adding to the selected honey. The contribution of the water in the silver nitrate solution in this instance is considered negligible and is estimated to be about 0.6% of the total mass of the silver nitrate solution.

In short then, it should be understood that silver nitrate in combination with medical grade honey can be utilized for its anti-inflammatory effects and to encourage blood vessel formation; however, it should also be understood that silver alone does nothing in a wound except to damage bacteria. To be complete then, applicants have discovered that a combination of medical grade honey and silver nitrate in a ratio of between about 50 to 1 and about 1000 to 1 provides a power antibacterial action on an infected wound, and in addition, the combination provides protection from outside sources of biological contamination. A more preferred ratio is between about 200 to 1 and about 250 to 1, and the most preferred ratio is about 211 to 1 provides an unexpected antibacterial effect which is substantially greater than the antibacterial effect of either component taken alone when applied to a wound.

Considering now the honey and silver nitrate composition 14 in still greater detail, the preferred embodiment of the honey and silver nitrate composition 14 is prepared by the combination of a selected medical grade honey and silver ions ($Ag+$) provided in the form of silver nitrate ($AgNO_3$) to provide a gel-like composition 14, where the preferred honey to silver nitrate ratio is about 211 to 1. It is to be understood that when the honey and the silver nitrate are mixed together to form the gel-like composition 14, there is no chemical reaction between these components of the mixture. It is to be further understood that the combination of silver ions with medical grade honey provides powerful antibacterial forces on infected wounds and protection from outside sources of biological contamination. More particularly, silver compounds and honey damage bacteria in different ways. These different mechanisms of action in combination therefor, as made available in the composition of the present invention, provide an unexpected amplified antibacterial action for improved healing results. Moreover, silver nitrate unlike other salts of silver, such as silver chloride, silver acetate, and silver zeolite, facilitates the ability to incorporate a sufficient amount of silver nitrate into the honey whilst maintaining a honey moisture content of the composition at or below 20 percent. This is an important feature of the present invention as mentioned earlier, since by keeping the moisture level of the composition 14 at or below the 20 percent level, the growth of mold, mildew, fungus and yeast will be substantially prevented.

The composition 14 of the present invention requires the utilization of medical grade honey. In this regard, the most preferred medical grade honey is Manuka honey which is produced in New Zealand by bees that pollinate native Manuka bushes. Manuka honey is the most preferred honey since it provides larger quantities of methylglyoxal than can be found in other honeys. Manuka honey in this regard, has the ability to have a rapid deodorizing effect with patients having malodorous fumigating wounds, which could be due to the inhibition of anaerobic bacterial growth. Also, the high sugar levels in honey may well result in osmotic pressure that promotes autolytic debridement and, for these reasons, Manuka honey is the preferred honey for use in the composition. The terminology "osmotic pressure" is defined herein to mean the pressure required to maintain equilibrium of two solutions, with no net movement between one solution (e.g., a solvent) and the other solution. The terminology "autolytic debridement" is defined herein to mean a process by which the body's own enzymes and moisture are used to re-hydrate, soften and liquefy hard eschar and slough (i.e., dry scab and dead tissue).

Method of Preparing the Honey and Silver Nitrate Composition

The following example is provided merely for illustrating the present invention and is not to be intended as limiting the scope of protection of the appended claims.

Example 1

1.) Composition

A honey and silver nitrate composition has been formulated with the following composition:
a.) Batch size of honey could be between about one (1) gram and about 91,000 kg;
  i. Preferably, the batch size will be between about 900 kg and 1,800 kg of honey;
b.) The honey to silver nitrate ratio should be about 211:1.

2.) Method

The following steps were carried out:
a.) Heat the honey to 30° C. within a holding tank having built-in mixers;
b.) Mix in the silver nitrate with the honey
c.) Use the built-in mixers to blend the honey and silver nitrate;
d.) Pass the blended honey and silver nitrate mixture through an in-line high speed mixer;
  i. The settings of the high speed mixer are set to ensure that the honey and silver nitrate mixture is of a correct consistency (a gel-like solution) and fully homogenized to assure uniformity of the honey within the mixture; thus, reducing the potential for honey crystallization; and
e.) Pump the honey and silver nitrate mixture into a holding container for shipping to a bulk weight of the mixture 14 to a tube or dressing converter (25 kg bucket, 280 kg drum, 1 ton). For example, refer to FIG. 5 herein and the discussion related thereto for the preparation of a gap-patterned foam dressing 50.

3.) Test Results

The following tests were carried out:
a.) Log Reduction Tests
  i. The Log Reduction tests provide a quantitative measurement describing what percentage of the contaminants, which were present when the test began, was killed during the test and at what time.
  ii. The honey and silver nitrate composition 14 passed both tests.
b.) Methylglyoxal and Dihydroxyacetone (DHA) testing:
  i. The test is used to ensure that the natural antimicrobial properties within the honey (Methylglyoxal and DHA) were not impacted/diluted or attacked by the adding of silver salts, such as silver nitrate.
  ii. The honey and silver nitrate composition 14 passed the test.

Applications of the Honey and Silver Nitrate Composition

To begin, it should be mentioned that the honey silver nitrate composition 14 of the present invention may be included in any of the following dressing types: (1) A hydrocolloid wound dressing comprised of sodium carboxymethylcellulose, gelatin, pectin, elastomers, and adhesives bound to a carrier of semipermeable film or a foam sheet to produce a flat, occlusive, adhesive dressing that forms a gel on a wound surface, promoting moist wound healing; (2) a hydrogel wound dressing comprising a matrix of insoluble polymers with up to 96% water content enabling them to donate water molecules to the wound surface and to maintain a moist environment at the wound bed; (3) an alginate wound dressing produced from naturally occurring calcium and sodium salts of alginic acid found in a family of brown seaweed (Phaeophyceae); (4) SAF/SAP absorbent dressings; and (5) foam dressings. What follows therefore is an example of one of these types of dressings, which explanation is provided without limiting the application of the composition 14 to the other types of dressings.

Figure 1:
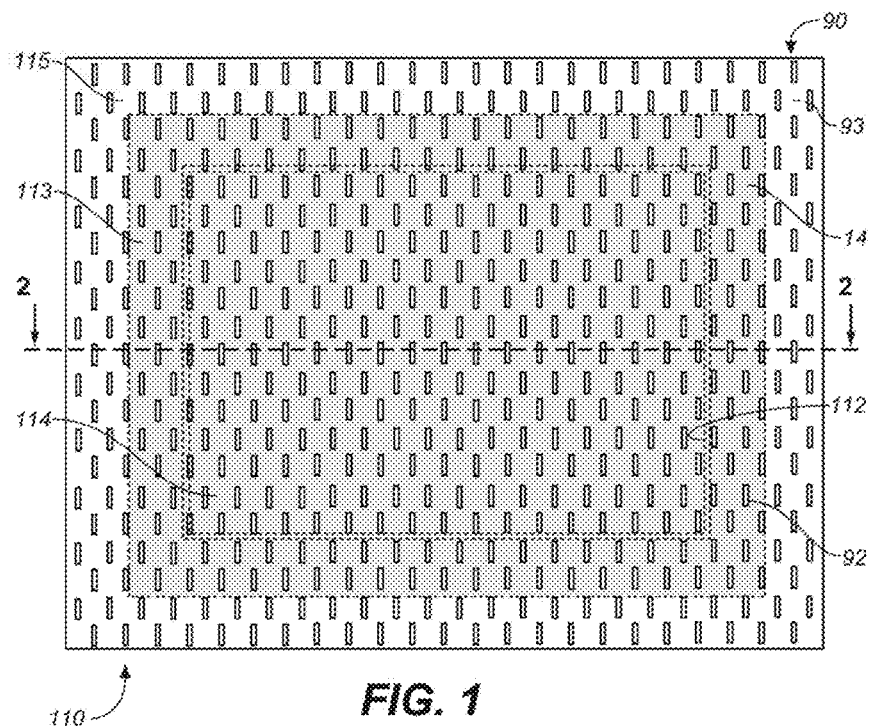
FIG. 1 is a top plane view of a medical grade dressing impregnated with a composition of honey and silver nitrate, which dressing is constructed in accordance with the present invention.
Figure 2:
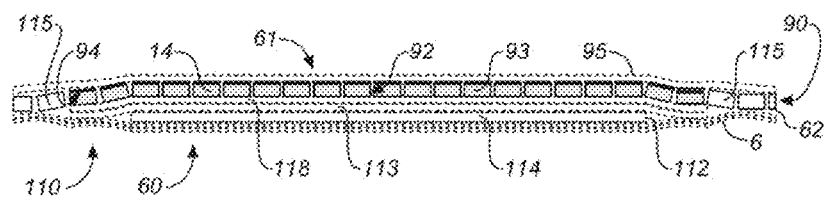
FIG. 2 is a cross-sectional view of the medical grade dressing of FIG. 1 taken substantially along line 2-2.

Referring now to the drawings and more particularly to FIGS. 1 and 2, there is illustrated a honey and silver nitrate impregnated medical grade dressing 110, which is constructed in accordance with the present invention. As described in more detail herein below, honey silver nitrate impregnated gauze dressing 110, has a non-wound contact side indicated generally at 60 (FIG. 2) and a wound contact side indicated generally at 61 (FIG. 2), comprises a material, such as gauze, which contains gaps in the gauze, in combination with an absorbent pad located in a pouch attached to the gauze. The surface of the gauze is dosed with the honey silver nitrate composition 14, such that the honey silver nitrate composition 14 resides within the gauze around the gaps. In use, the side of the dressing 110 containing the honey silver nitrate composition 14 is placed on the wound to promote healing of the wound. An anti-tackiness coating, sheet or protective layer may or may not cover the honey silver nitrate composition.

The honey silver nitrate impregnated gauze dressing 110 exhibits several advantages. As stated herein above, the gauze contains the honey silver nitrate within its structure. The gaps in the gauze allow for greater conformity and flexibility of the dressing. Furthermore, the gaps allow for the free passage of exudate from the wound, so that this can be collected and managed by the absorbent pad located within the pouch underneath the honey silver nitrate impregnated gauze. The absorbent pad contains super absorbent powder to manage high levels of exudate, locking it within the secure pouch. The choice of the material for the wicking layer which forms one side of the pouch, between the honey silver nitrate impregnated gauze and the absorbent pad, allows a slow initial transfer of exudate which thereby reduces the risk of painful wound treatment often associated with the application of super absorbent dressings. Maintaining a steady rate of transfer of exudate promotes the complete dispersal of the composition 14 throughout the wound treatment zone. Also, honey silver nitrate impregnated gauze dressing 110 includes a protective cover and a picture frame dry edge for ease of handling during application (FIG. 2). Finally, as previously discussed herein, the high sugar levels found in the honey, result in an osmotic pressure that promotes autolytic debridement.

Referring back to FIGS. 1-2, the honey silver nitrate impregnated gauze dressing 110 will now be described. In this regard, and with reference to FIG. 1, the honey silver nitrate impregnated gauze dressing 110 may be constructed with either a single ply or triple ply gauze material, such as a gauze material 90. A pouch 112 is formed from an adhesive coated wicking layer 113 and a polyurethane barrier 6, which forms the backing to dressing 110. Inside the pouch 112, an absorbent pad 114 is located to collect and manage exudate from the wound. The wicking layer 113 has an acrylate adhesive 118 which has the necessary wet performance properties to regulate the flow of exudate through the dressing.

Gauze 90 is woven, knitted or structured so as to define a plurality of laterally adjacent linear shaped gaps 92 therein, illustrated with white background. Gaps 92 form a regular pattern similar to the parallel walls between the cells on a honey comb. In this manner, honey silver nitrate impregnated gauze dressing 110 forms a matrix that may be considered analogous to the structure of a bee's honey comb.

The honey silver nitrate composition 14 is disposed into gauze 90 in fabric 93 to completely fill the structure apart from the gaps and the picture frame dry edge feature shown more clearly in FIG. 1. For clarity of understanding the gauze dressing 110, the honey silver nitrate composition 14 is shown in FIG. 1 as unobstructed shaded areas. The honey silver nitrate composition 14 is used, among other things, to reduce the risk of wound infection and to promote healing. The preferred weight of honey silver nitrate dose for this presentation is between 40-66% of the total dressing weight depending upon the gauze ply being utilized. See Table I for specific weight percentages.

Finally, it is to be understood that dressing 110 may or may not include dry edges, such as the dry edges 115. Located on the wound contact face 61 of dressing 110 is an anti-tackiness coating, sheet or layer 94 and an additional protective cover 95 over the honey silver nitrate impregnated fabric 93. Anti-tackiness coating, sheet or layer 94 will reduce the risk that dressing 110 will undesirably adhere to the wound site. In this regard, anti-tackiness layer 94 should have a low stickiness property (i.e., low ability to retain solvents upon drying). Such an anti-tackiness layer 94 may comprise silicone oil, or other suitable anti-tackiness compositions. It is to be understood that the anti-tackiness layer 94 may be eliminated in order to reduce manufacturing costs, without affecting the functionality of dressing 110, due to the surface texture of the gauze 90. In summary then, the above-described honey silver nitrate impregnated dressing 110 is used, amongst other things, to reduce bacterial colonization, to facilitate autolytic debridement of the wound, to reduce the wound pH levels, to decrease wound odor, to help support a moist wound healing environment, and to help absorb wound exudate.

Table I, as illustrated below, provides an indication of the different types of base materials that may be utilized in preparing a honey silver nitrate wound dressing. It should be understood by those skilled in the art that such wound dressing may be provided in a plurality of different sizes and can be easily cut to provide a dressing of a standard medical size. It should be further understood that the selected gauze preferably is a woven, knitted or structured configuration in order to be able to adequately retain the honey and silver nitrate composition 14 until the dressing 110 is ready to be applied to a wound. Also, the selected gauze should not come apart, lint or fray and should be constructed with an open cell structure.

TABLE I

| Base Dressing Material | Weight (grams/square meter) | % of Composition by Weight |
|---|---|---|
| Single ply gauze | about 100 | about 40-60% |
| Triple ply gauze | about 300 | about 52-66% |
| Foam | between about 300 and 500 | about 44-60% |

With respect FIG. 3, while in the preferred embodiment of the present invention, a honey silver nitrate impregnated gauze dressing 110 has been illustrated, it should be appreciated by those skilled in the art, that the honey and silver nitrate composition 14 of the present invention may also be placed within a tube assembly, such as a tube assembly 30. Placing the composition 14 within such as a tube assembly 30, provides an added ease of use benefit. Moreover, as will be explained hereinafter in greater detail, the tube assembly 30 may be manipulated between an open and closed position facilitating direct wound or direct wound dressing application of the composition 14.

Considering now the tube assembly 30 in greater detail, the tube assembly 30 generally includes a tube 32 having retained thereon a re-closable cap 36. The tube 32 is configured for holding a fixed quantity of the honey and silver nitrate composition 14 with a gel-like consistency. As best seen in FIG. 3, the tube 32 has an open proximal end, indicated generally at 31, and a sealed distal end, indicated generally at 33. The open proximal end 31 is configured for receiving thereon the re-closable cap 36. In this regard, the re-closable cap 36 when rotated about its longitudinal axis by about 270 degrees in a counterclockwise direction opens to provide an exit passageway extending from the interior of the tube 32 to the proximal end of the re-closable cap 36 to allow a portion of the gel-like honey and silver composition 14 to be expelled out of the tube 32 and through the opened passage of the cap for application to a wound or wound dressing whichever is the case, as best seen in FIG. 3. When the re-closable cap 36 is rotated in an opposite clockwise direction about its longitudinal axis by 270 degrees from the open position, the cap 36 is positioned in a closed position preventing any portion of the honey and silver nitrate composition 14 from being expelled from the tube 32.

The tube 32 is constructed of any suitable, durable, medical grade metallic or polymeric material which will allow the honey and silver composition 14 to be expelled out of tube end 34 through the re-closable cap 36, as previously described, when the cap 36 is rotated to its open position and pressure is applied along a portion of tube 32. The proximal tube end 31 is, preferably, constructed with a threaded exterior portion (not shown) that interacts with the cap 36 in order to retain the cap 36 on the exterior portion at all times. In this regard, this configuration allows the cap 36 to be rotated between its closed position and its open position, as previously described. Finally, re-closable cap 36 is constructed of any suitable, durable, medical grade metallic or polymeric material which includes a conventional threaded interior portion that is capable of interacting with the threaded exterior portion of tube end 31. It should be further understood by those skilled in the art that a conventional removable cap may also be employed when the tube 32 is constructed in a disposable single dose size.

Tube assembly 30, when opened, allows the gel-like, honey and silver nitrate composition 14 to be applied directly to a wound (W) by conventional techniques used to apply other wound treatment compositions. However, it is to be understood that the amount of composition 14 used on such a wound (W) would be determined by wound factors, such as the size, type, depth and degree of wound infection one would observe with respect to the wound.

It is to be understood that the consistency of composition 14 remains the same across all product variants in that the same composition 14 is used in both gauze dressing 10 and as a composition applied directly to the wound or medical grade dressing 20 (FIG. 4).

With respect to composition 14 and tube assembly 30, it should also be understood that composition 14 can be used in the following applications and uses which include, but are not limited to, prescription applications and/or uses such as leg ulcers, pressure ulcers, first and second degree burns, diabetic foot ulcers, surgical wounds, trauma wounds, and partial & full thickness wounds. Also, composition 14 can be used in over the counter applications and/or uses such as minor abrasions, lacerations, minor cuts, and minor scalds and burns.

Finally, it is to be understood that composition 14 can be used in the following technologies which include, but are limited to, tubes of various sizes, sachets and pouches of various sizes, gauze material of various sizes, foam material of various sizes, hydrocolloid mixes of various sizes, hydrogel mixes of various sizes, alginate mixes of various sizes, and super absorbent material (SAF/SAP) of various sizes. It being understood by those skilled in the art that hydrocolloids, hydrogels, and alginates are all wound dressings that help maintain a moist wound healing environment.

Figure 5:
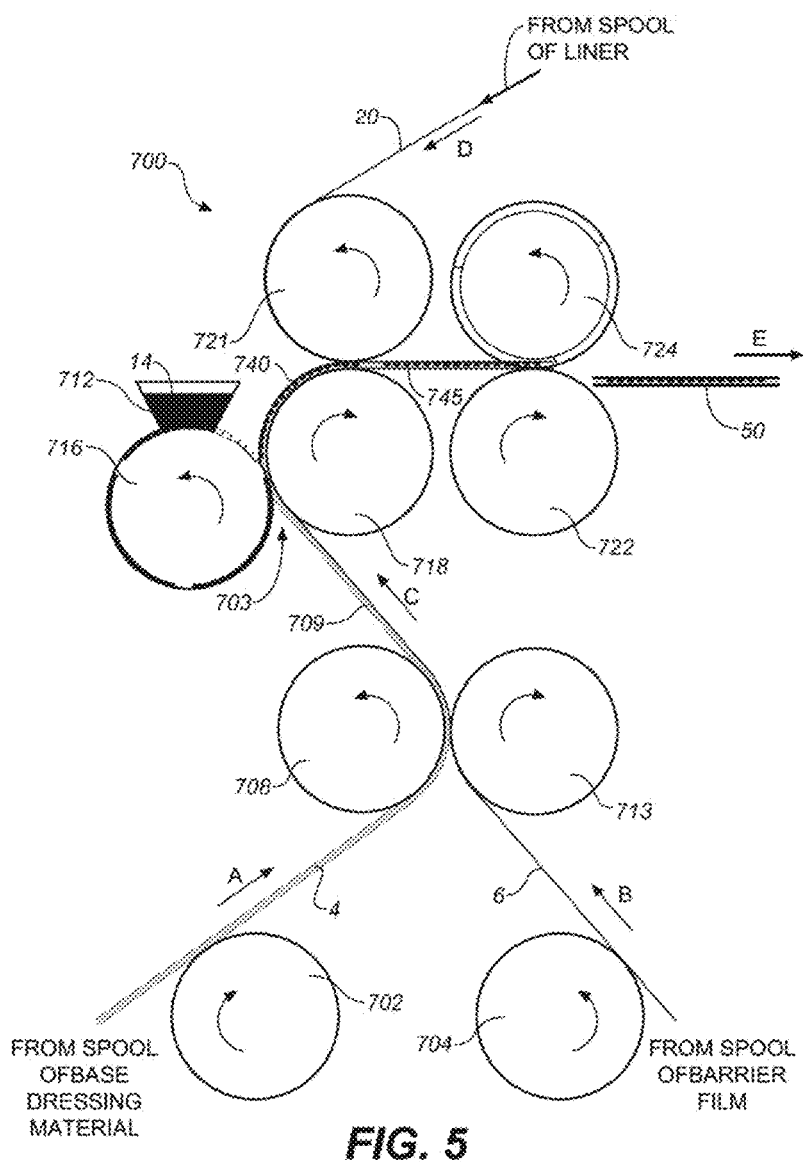
FIG. 5 is a schematic illustration of the construction of a medical grade dressing, constructed according to the present invention.

Considering now the method of constructing a honey silver nitrate dressing 50, reference should be made to FIG. 5 which illustrates a manufacturing apparatus 700 for preparing a gap patterned foam dressing dosed or impregnated with the honey and silver nitrate composition 14 of the present invention. The method of preparing a gap patterned foam dressing with a medical grade honey alone, is more fully described in U.S. Pat. No. 9,107,974, which is incorporated herein as though fully set forth. For the purpose of the present disclosure, it should be noted that the only difference between the present foam dressing 50 and the one described in the above-mentioned U.S. Pat. No. 9,107,974, is that the present dressing 50 utilizes the honey silver nitrate composition 14 of the present invention as opposed to a pure medical grade honey as was described relative to U.S. Pat. No. 9,107,974. But for that difference, the manufacturing processes are substantially identical.

Referring now to FIG. 5, it can be seen that the manufacturing apparatus 700 generally includes a first set of feed rollers indicated at 702 and 704, respectively. Feed roller 702 pulls into a construction path (A) a ribbon of base material 4, such as a foam material (as described in this instance) or gauze material (when constructing gauze impregnated dressings, such as the gauze impregnated dressing 110 as best seen in FIGS. 1-2. The foam base dressing material 4 is pulled from a spool of the base dressing material (which spool is not shown). The ribbon of base material 4 has a width dimension which is required for the dressing 50. Feed roller 704 pulls into another construction path (B), a ribbon of barrier material 6, whose width dimension corresponds to the width dimension of the base material 4. The A construction path and the B construction path merge at the nip of a pair of laminating rollers 708 and 713, respectively. In this regard, the base material 4 and the barrier material 6 traverse along the direction of the construction paths A and B, respectively wherein the base material 4 and the barrier material 6 are laminated together between the conventional laminating rollers 708 and 713 to create lamination 709. The laminating rollers 708 and 713 then cooperate with a pair of upstream rollers, namely a heated form roller 716 and a drive roller 718.

As best seen in FIG. 5, the heated form roller 716 is in fluid contact with a reservoir 712 of the honey silver nitrate composition 14 which is constructed in accordance with the present invention. In this regard, when the surface of roller 716 passes by the reservoir 712, the conventionally heated roller 716 withdraws a predetermined amount of honey 14 from reservoir 712. It is to be understood that reservoir 712 can be located at other positions in apparatus 700. The honey coated roller 716 and drive roller 718 then engage the lamination 709 at their nip 703 which doses the barrier free side of lamination 709 with a sufficient amount of the honey silver nitrate composition 14 to establish a composition to base material weight in accordance with the type of base material being utilized and as more fully shown in Table I. In the present disclosure, since the base material is the foam base material 4, the percentage weight of the honey silver nitrate composition to the total base material weight is between about 44% and about 60%. It should be understood by those skilled in the art, that the reservoir 712 can be located at other positions within the apparatus 700, The composition coated roller 716 and drive roller 718 then engage the lamination 709 at their nip 703 which dose the foam side of the lamination 709 such that a patter pattern of composition-dosed foam areas and a pattern of gap foam areas or wall are created in the base material 4. A thin micro or minimal trace layer (not shown) of the honey silver nitrate composition 14 is deposited on the surface of the patterned surface of the patterned dosed foam 740 as it emerges from between rollers 716 and 718, respectively.

As the gap-patterned foam 740 emerges from between the heated form roller 716 and drive roller 718, it is further pulled upstream by a feed roller 721 which helps drive a liner 20 into a nip between the drive roller 718 and the feed roller 721 so that liner 20 is applied to the wet surface of the gap-patterned foam 740 to form a liner covered gap-patterned foam ribbon, indicated generally at 745. In this manner, liner 20 is retained on gap-patterned foam 740 by the micro or minimal trace layer of the honey silver nitrate composition.

Next, ribbon 745 is pulled upstream by a drive roller 722 and a conventional rotary tool roller 724 which cooperate for die cutting the liner covered gap-patterned foam ribbon 745 as ribbon 745 passes between rollers 722 and roller 724, where it emerges as the dressing 50. It is to be understood that all rollers, as mentioned herein turn at substantially the same surface speed as lamination 709, which can be anywhere between 1 m/minute and 15 m/minute. After exiting from the rotary tool roller 724, the dressing 50 then passes into a packaging mechanism (not shown) which packages individual ones of the dressing 50 in a pouch 80 package for ease of handling and radiation sterilization.

The preceding merely illustrates the principles of the invention. It will thus be appreciated that those skilled in the art will be able to devise various arrangements which, although not explicitly described or shown herein, embody the principles of the invention and are included within its spirit and scope. Furthermore, all examples and conditional language recited herein are principally intended expressly to be only for pedagogical purposes and to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently known equivalents and equivalents developed in the future, i.e., any elements developed that perform the same function, regardless of structure.

This description of the exemplary embodiments is intended to be read in connection with the figures of the accompanying drawing, which are to be considered part of the entire written description. In the description, relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents to the extent such incorporated materials and information are not inconsistent with the description herein.

The written description portion of this patent includes all claims. Furthermore, all claims, including all original claims as well as all claims from any and all priority documents, are hereby incorporated by reference in their entirety into the written description portion of the specification, and Applicant(s) reserve the right to physically incorporate into the written description or any other portion of the application, any and all such claims. Thus, for example, under no circumstances may the patent be interpreted as allegedly not providing a written description for a claim on the assertion that the precise wording of the claim is not set forth in haec verba in written description portion of the patent.

The claims will be interpreted according to law. However, and notwithstanding the alleged or perceived ease or difficulty of interpreting any claim or portion thereof, under no circumstances may any adjustment or amendment of a claim or any portion thereof during prosecution of the application or applications leading to this patent be interpreted as having forfeited any right to any and all equivalents thereof that do not form a part of the prior art.

All of the features disclosed in this specification may be combined in any combination. Thus, unless expressly stated otherwise, each feature disclosed is only an example of a generic series of equivalent or similar features.

It is to be understood that while the invention has been described in conjunction with the detailed description thereof, the foregoing description is intended to illustrate and not limit the scope of the invention, which is defined by the scope of the appended claims. Thus, from the foregoing, it will be appreciated that, although specific embodiments of the invention have been described herein for the purpose of illustration, various modifications may be made without deviating from the spirit and scope of the invention. Other aspects, advantages, and modifications are within the scope of the following claims and the present invention is not limited except as by the appended claims.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by various embodiments and/or preferred embodiments and optional features, any and all modifications and variations of the concepts herein disclosed that may be resorted to by those skilled in the art are considered to be within the scope of this invention as defined by the appended claims.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

It is also to be understood that as used herein and in the appended claims, the singular forms "a," "an," and "the" include plural reference unless the context clearly dictates otherwise, the term "X and/or Y" means "X" or "Y" or both "X" and "Y", and the letter "s" following a noun designates both the plural and singular forms of that noun. In addition, where features or aspects of the invention are described in terms of Markush groups, it is intended and those skilled in the art will recognize, that the invention embraces and is also thereby described in terms of any individual member or subgroup of members of the Markush group.

Other embodiments are within the following claims. Therefore, the patent may not be interpreted to be limited to the specific examples or embodiments or methods specifically and/or expressly disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

Other modifications and implementations will occur to those skilled in the art without departing from the spirit and the scope of the invention as claimed. Accordingly, the description hereinabove is not intended to limit the invention, except as indicated in the appended claims.

Therefore, provided herein are a new and improved honey and silver nitrate composition and dressing and a novel method of preparing the honey and silver nitrate composition. The preferred honey and silver nitrate composition and dressing, according to various embodiments of the present invention, offer the following advantages: ease of use of the composition; ease of application of the composition to a wound dressing; excellent light and heat stability of the composition; excellent osmotic absorption of excess exudate by the dressing during treatment; excellent anti-bacterial activity of the composition; excellent hygroscopic characteristics of the composition; the ability of the composition to provide nutrients to the wound bed; excellent anti-inflammatory characteristics of the composition; excellent pain relieving characteristics of the composition; reduced healing time of the wound; excellent debridement characteristics of the composition; increased antimicrobial characteristics of the composition; and improved odor control by the composition. In fact, in many of the preferred embodiments, these factors of ease of use, ease of application of the composition to a wound dressing, excellent light and heat stability of the composition, excellent osmotic absorption of excess exudate by the dressing during treatment, excellent anti-bacterial activity of the composition, excellent hygroscopic characteristics of the composition, the ability of the composition to provide nutrients to the wound bed, excellent anti-inflammatory characteristics of the composition, excellent pain relieving characteristics of the composition, reduced healing time of the wound; excellent debridement characteristics of the composition, increased antimicrobial characteristics of the composition, and improved odor control of the composition are optimized to an extent that is considerably higher than heretofore achieved in prior, known honey and silver nitrate compositions and dressings.

We claim:

1. A composition for treating burns, ulcers and wounds, comprising:
a mixture of sterilized honey and a dissolved silver ion salt in a preferred sterilized honey to silver ion salt ratio of between 200 to 1 and 250 to 1,
wherein the sterilized honey has a moisture content of between one and twenty percent; and
wherein the sterilized honey contains a preferred amount of methylglyoxal of between 83 milligrams of methylglyoxal per 1.0 kilogram of sterilized honey and 1000 milligrams of methylglyoxal per 1.0 kilogram of sterilized honey.

2. The composition, according to claim 1, wherein a more preferred sterilized honey to silver salt ion ratio is 211 to 1; and
a more preferred amount of methylglyoxal is between 300 milligrams of methylglyoxal per 1.0 kilogram of sterilized honey and 350 milligrams of methylglyoxal per 1.0 kilogram of sterilized honey.

3. The composition, according to claim 1, wherein the dissolved silver ion salt is a dissolved silver nitrate salt.

4. The composition, according to claim 2, wherein the dissolved silver ion salt is a dissolved silver nitrate salt.

5. The composition, according to claim 3, wherein the mixture of sterilized honey and dissolved silver nitrate salt is a gel.

6. The composition, according to claim 1, wherein the sterilized honey is selected from a group consisting of: Manuka, Pasture, Ling Kahami, Portobello, Greek Pine, Yorkshire, Chilean Ulmo, Chilean Rain Forrest, Australian *Eucalyptus*, Himalayan, Scottish Heather, Scottish Wild Flower, English Heather, English Wildflower, New Zealand Clover, Australian Clover, Cuban Comparitan, *Acacia*, Spanish Blossom, Tasmanian Leatherwood, Organic Honey All, New Zealand Beach, Kanuka, New Zealand Bush, New Zealand Honey Dew, Jarrah, Thyme, Kamahi and *Leptospermum* honeys of all varieties.

7. A method of preparing a sterilized honey and silver nitrate composition for treating wounds, comprising the steps of:
heating an amount of sterilized honey, wherein the sterilized honey contains a preferred amount of methylglyoxal of between 83 milligrams of methylglyoxal per 1.0 kilograms of sterilized honey and 1000 milligrams of methylglyoxal per 1.0 kilogram of sterilized honey;
mixing an amount of sterile water with an amount of silver nitrate to dissolve the amount of silver nitrate in the sterile water;
blending the mixture of dissolved silver nitrate and sterile water with the amount of heated sterilized honey while maintaining, a honey moisture content of between one and twenty percent;
placing the blended sterilized honey and the silver nitrate into a high speed mixer; and
mixing the blended sterilized honey and the silver nitrate in the mixer until a fully homogenized composition of sterilized honey and silver nitrate is achieved.

8. The method of preparing a sterilized honey and silver nitrate composition, according to claim 7, wherein the step of blending includes:
maintaining a preferred ratio of sterilized honey and silver nitrate of between 200 to 1 and 250 to 1.

9. The method of preparing a sterilized honey and silver nitrate composition, according to claim 8, wherein a more preferred sterilized honey to silver nitrate ratio is 211 to 1; and
wherein a more preferred amount of methylglyoxal is between 300 milligrams of methylglyoxal per 1.0 kilogram of sterilized honey and 350 milligrams of methylglyoxal per 1.0 kilogram of sterilized honey.

10. The method of preparing a sterilized honey and silver nitrate composition, according to claim 9, wherein the step of heating includes: heating the amount of sterilized honey to about 30° C.

11. The method of preparing a sterilized honey and silver nitrate composition, according to claim 7, wherein the step of heating includes: heating the amount of sterilized honey to about 30° C.

12. The method of preparing a sterilized honey and silver nitrate composition, according to claim 7, wherein the sterilized honey is selected from a group consisting of: Manuka, Pasture, Ling Kahami, Portobello, Greek Pine, Yorkshire, Chilean Ulmo, Chilean Rain Forrest, Australian *Eucalyptus*, Himalayan, Scottish Heather, Scottish Wild Flower, English Heather, English Wildflower, New Zealand Clover, Australian Clover, Cuban Comparitan, *Acacia*, Spanish Blossom, Tasmanian Leatherwood, Organic Honey All, New Zealand Beach, Kanuka, New Zealand Bush, New Zealand Honey Dew, Jarrah, Thyme, Kamahi and *Leptospermum* honeys of all varieties.

13. A composition for treating burns, ulcers and wounds, comprising:
   a volume of sterilized honey containing a preferred amount of methylglyoxal of between 83 milligrams of methylglyoxal per 1.0 kilogram of sterilized honey and 1000 milligrams of methylglyoxal per 1.0 kilogram of sterilized honey;
   a volume of dissolved silver nitrate in a sufficient volume to provide a mixture of sterilized honey and silver nitrate in a ratio of between 200 to 1 to 250 to 1 and;
   wherein the sterilized honey has a moisture content of between one and twenty percent to facilitate inhibiting the growth of mold, mildew, fungus and yeast.

14. The composition for treating burns, ulcers and wounds, according to claim 13, wherein a more preferred sterilized honey to silver nitrate ratio is 211 to 1; and a more preferred amount of methylglyoxal is between 300 milligrams of methylglyoxal per 1.0 kilogram of sterilized honey and 350 milligrams of methylglyoxal per 1.0 kilogram of sterilized honey.

15. The composition for treating burns, ulcers and wounds, according to claim 13, wherein the sterilized honey is selected from a group consisting of:
   Manuka, Pasture, Ling Kahami, Portobello, Greek Pine, Yorkshire, Chilean Ulmo, Chilean Rain Forrest, Australian *Eucalyptus*, Himalayan, Scottish Heather, Scottish Wild Flower, English Heather, English Wildflower, New Zealand Clover, Australian Clover, Cuban Comparitan, *Acacia*, Spanish Blossom, Tasmanian Leatherwood, Organic Honey All, New Zealand Beach, Kanuka, New Zealand Bush, New Zealand Honey Dew, Jarrah, Thyme, Kamahi and *Leptospermum* honeys of all varieties.

16. The composition for treating burns, ulcers and wounds, according to claim 13, wherein the mixture of sterilized honey and silver nitrate is a gel.

* * * * *